United States Patent [19]
Yagi et al.

[11] Patent Number: 5,523,020
[45] Date of Patent: Jun. 4, 1996

[54] CLATHRATE COMPOUND INCLUDING WATER-SOLUBLE MICROBICIDE

[75] Inventors: Minoru Yagi; Kazumi Nakane; Yuriko Hiyane, all of Tokyo, Japan

[73] Assignee: Kurita Water Industries Ltd., Tokyo, Japan

[21] Appl. No.: 309,179

[22] Filed: Sep. 20, 1994

[30] Foreign Application Priority Data

Oct. 1, 1993 [JP] Japan ................... 5-246888

[51] Int. Cl.$^6$ .................. A01N 43/80; C07D 275/03
[52] U.S. Cl. .................. 252/404; 514/372; 548/213
[58] Field of Search .................. 548/213; 514/372; 252/404

[56] References Cited

U.S. PATENT DOCUMENTS

| | | | |
|---|---|---|---|
| 4,973,700 | 11/1990 | Sekikawa et al. | 548/213 |
| 5,082,654 | 1/1992 | Sugi et al. | 514/617 |
| 5,133,969 | 7/1992 | Sekikawa et al. | 424/416 |

FOREIGN PATENT DOCUMENTS

| | | |
|---|---|---|
| 0327214 | 8/1989 | European Pat. Off. . |
| 0326262 | 8/1989 | European Pat. Off. . |
| 0326261 | 8/1989 | European Pat. Off. . |

OTHER PUBLICATIONS

Chemical Abstracts, vol. 107:54214u; Jan. 19, 1987.
Database WPI, Section Ch, Week 9203, Derwent Publications Ltd., Class D22, AN 92-021493 & JP-A-03 271 204 (Kureita Water Ind KK), Dec. 3, 1991.
Database WPI, Section Ch, Week 9204, Derwent Publications Ltd., Class C02, AN 92-030653 & JP-A-03 279 373 (Kurita Water Ind KK), Dec. 10, 1991.

*Primary Examiner*—Johann Richter
*Assistant Examiner*—Laura R. Cross
*Attorney, Agent, or Firm*—Kanesaka & Takeuchi

[57] ABSTRACT

A clathrate compound composed of a water-soluble microbicide and a phenolic compound of formula (1) or (2):

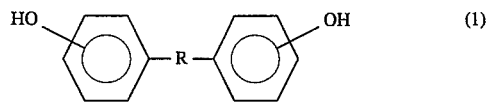

(R: 2-4C alkylidene)

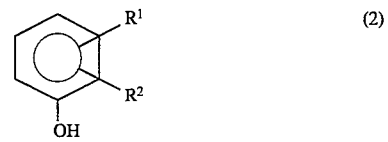

10 Claims, No Drawings

CLATHRATE COMPOUND INCLUDING WATER-SOLUBLE MICROBICIDE

FIELD OF THE INVENTION AND RELATED ART STATEMENT

The present invention relates to a clathrate compound and, more particularly, to a novel clathrate compound including a water-soluble microbicide, which improves the handleability and the stability of the microbicide therein.

In water systems such as cooling water systems in various factory plants or the pulp and paper industries, slime of various bacteria, fungi, animals and vegetables adheres to the ducts or lines to cause various problems.

Hitherto, for the purpose of preventing the problems caused by slime or the like in such systems, a microbicide (slime-controlling agent) has generally been employed as it is easily handled, and it is relatively inexpensive. For instance, 5-chloro-2-methyl- 4-isothiazolin-3-one of the following formula (I) (hereinafter referred to as "Cl-MIT") is widely used as a slime-controlling agent, a bactericide, an algicide or a fungicide for various water systems such as a cooling water system, a papermaking process system or a swimming pool, as it has an excellent microbicidal activity.

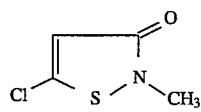

(I)

However, Cl-MIT is extremely stimulative to the skin and caution is necessary when handling the same, though it has an excellent microbicidal activity.

Since Cl-MIT decomposes extremely easily, water-soluble microbicides on the market contain a Large amount of Mg salts so as to stabilize Cl-MIT therein. Therefore, such commercial microbicides cannot be employed in the field of latex and emulsion which do not accept Mg salts.

Cl-MIT can be separated from the water-soluble microbicides on the market by extraction methods using organic solvents, but the thus-extracted Cl-MIT is unstable especially under heat, so that it decomposes within one or two days even at a temperature of about 40° C. For these reasons, special storage conditions are necessary such as storing the compound in a refrigerator.

In order to overcome problems such as above, the present applicant has already proposed clathrate compounds having a water-soluble microbicide such as Cl-MIT containing a host compound such as a bisphenol halide (Japanese Patent Laid-Open Publication No. 1-190602).

Among the host compounds proposed in Japanese Patent Laid-Open Application No. 1-190602, 2,2'-methylenebis(4-chlorophenol) has been considered preferred.

OBJECT AND SUMMARY OF THE INVENTION

It is an object of the present invention to provide an improved clathrate compound including a water-soluble microbicide such as Cl-MIT.

The clathrate compound of the present invention is characterized by comprising a water-soluble microbicide and a phenolic compound of the following general formula (1) or (2):

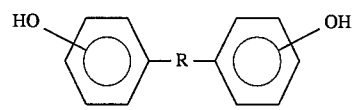

(1)

wherein R represents an alkylidene group having from 2 to 4 carbon atoms.

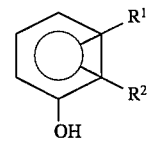

(2)

wherein each of $R^1$ and $R^2$ represents an alkyl group having from 2 to 4 carbon atoms.

As the water-soluble microbicide, preferred is Cl-MIT having the above-mentioned structural formula (I).

Specifically, the clathrate compound of the present invention is composed of a water-soluble microbicide such as Cl-MIT, as the guest compound, and the above-mentioned phenolic compound, as the host compound, wherein the host compound includes the guest compound therein.

DESCRIPTION OF THE PREFERRED EMBODIMENTS

Bisphenolic compounds of formula (1) to be used in the present invention include, for example, 4,4'-ethylidenebisphenol, 2,4'-isopropylidenebisphenol, 2,2'-vinylidenebisphenol, 4,4'-isobutylidenebisphenol, 2,6'-sec-butylidenebisphenol, etc.

Phenolic compounds of formula (2) also to be used in the present invention include, for example, 2,4-di-tert-butylphenol, 2,6-di-tert-butylphenol, 2,4-di-propylphenol, 2-propyl-4-tert-butylphenol, etc.

The water-soluble microbicide for use in the present invention may be any one that may form a clathrate compound with the above-mentioned phenolic compound. Cl-MIT which is widely used as an effective microbicide is preferable, but this is not limitative.

The clathrate compound of the present invention, comprising such a water-soluble microbicide and a phenolic compound, may easily be prepared by reacting them in an organic solvent or in water.

When an organic solvent is used for preparing it, a solution, which is prepared by dissolving any of the above-mentioned phenolic compounds in an ordinary organic solvent such as methanol, ethanol or acetone is mixed with a water-soluble microbicide such as Cl-MIT or with a mixture containing a water-soluble microbicide such as Cl-MIT and some impurities, etc., and reacted with the water-soluble microbicide. Accordingly, the intended clathrate compound precipitates out as a solid product, which is filtered and separated by ordinary methods.

When water is used for the same, the above-mentioned phenolic compound is directly added to an aqueous solution containing a water-soluble microbicide as the guest compound, and mixed by stirring. The aqueous solution to be used is not limited to one containing only a water-soluble microbicide as the guest compound. As in the above-mentioned case using an organic solvent, the solution may contain some impurities. The above-mentioned phenolic compound reacts with a water-soluble microbicide with high selectivity. Therefore, even when a water-soluble microbicide containing impurities such as side products is used directly as the raw meterial, a desired clathrate compound including selectively only the intended water-solube microbicide is obtained.

The reaction temperature may range from 0° C. to 100° C. In general, it is approximately from 10° C. to 30° C. The reaction time is from about 0.5 to 24 hours.

After the reaction, the clathrate compound is generally obtained as a solid product, which may be separated from the aqueous phase, washed with water and dried. Thus, the intended clathrate compound of the present invention is obtained.

The molar ratio between the water-soluble microbicide such as Cl-MIT and the above-mentioned phenolic compound of formula (1) both constituting the clathrate compound of the present invention, is generally such that (water-soluble microbicide):(phenolic compound (1)) is from 1:0.2 to 1:5. The molar ratio between the water-soluble microbicide such as Cl-MIT and the above-mentioned phenolic compound of formula (2), both constituting the clathrate compound of the present invention, is generally such that (water-soluble microbicide):(phenolic compound(2)) is from 1:0.2 to 1:5.

The clathrate compound of the present invention, thus obtained in the manner mentioned above, is generally powdery and may easily be shaped into tablets. Since the water-soluble microbicide is included as the host compound, the clathrate compound is low in toxicity and is easily handled, and the microbicide is prevented from reacting with other substance to lower its microbicidal activity during its use.

When the clathrate compound of the present invention is put into water, the water-soluble microbicide in the clathrate compound is released slowly therefrom. For example, when a clathrate compound of the present invention including 3% by weight of Cl-MIT therein is put into water, the amount of Cl-MIT to be released from the clathrate compound into water is as low as several 100 mg/liter. Therefore, a water-dispersible product containing a clathrate compound of the invention having the above-mentioned Cl-MIT concentration (3% by weight) is extremely preferred, as its stimulation to the skin is lessened. The compound of the present invention may be applied to a slow-release microbicide which slowly releases its active ingredient therefrom. Moreover, Since the clathrate compound of the present invention includes a water-soluble microbicide such as Cl-MIT as its guest compound, the microbicide therein is stabilized against heat.

The clathrate compound of the present invention may be used, for example, according to the methods mentioned below.

(1) The compound is packed in a column, and a liquid to be treated is passed therethrough.

(2) The compound is put into a bag or a cartridge which is permeable to water but does not dissolve in water, and the bag or cartridge is dipped in or floated above water systems.

(3) The compound of powder or tablet is dispersed in water systems.

(4) The compound is mixed with coating compositions, resins, etc., and the mixture is coated onto the surfaces of a device to be used in water systems, etc.

(5) The compound is adhered to the surfaces of the objects to be protected, by any suitable means.

It is preferred that the clathrate compound of the present invention is added to water to be treated in an amount of from 0.00001 to 0.5% by weight in terms of the concentration of the water-soluble microbicide such as Cl-MIT included in the clathrate compound.

The stability of the clathrate compound of the present invention is often poor in water, when it is added with no other additive. When a nitroalcoholic compound is added to the clathrate compound of the present invention, then the stability of the compound in water may be elevated.

The nitroalcoholic compound to be used for this purpose includes, for example, 2-chloro-2-nitro-ethanol, 1-chloro-1-nitro-2-propanol, 3-chloro-3-nitro-2-butanol, 2-chloro-2-nitro-1,3-butanediol, 1-chloro-1-nitro-2-butanol, 2-chloro-2-nitro-butanol, 2-chloro-2-nitro-3-pentanol, 2,2-dichrolo-2-nitro-ethanol, 2-bromo-2-chloro-2-nitro-ethanol, 3-chrolo-3-nitro-2,4-pentanediol, 4-chrolo-4-nitro-3-hexanol, 2-bromo-2-nitro-ethanol, 2-bromo-2-nitro-3-propanol, 2-bromo-2-nitro-1,3-butanediol, 3-bromo-3-nitro-2,4-pentanediol, 2,2-dibromo-2-nitro-ethanol, 1,1-dibromo-1-nitro-2-propanol, 4-bromo-4-nitro-3-hexanol, 2-fluoro-2-nitro-ethanol, 2-fluoro-2-nitro-1,3-butanediol, 3-Iodo-3-nitro-2-butanol, 2-chloro-2-fluoro-2-nitro-ethanol, 2-bromo-2-Iodo-2-nitro-ethanol, 2-chloro-2-nitro-1,3-propanediol, 2-bromo-2-nitro-1,3-propanediol. The amount of the compound to be added to the clathrate compound of the present invention is preferably from 0.1 to 5% by weight relative to the clathrate compound. If it is less than 0.1% by weight, a sufficient stabilizing effect cannot be attained. However even if it is more than 5% by weight, no difference in the stability-improving effect will be observed and therefore, such excess addition is not economical.

When a microbicidal composition comprising the clathrate compound of the present invention and such a nitroalcoholic compound is added to water to be treated therewith, it is preferred that the amount of the composition to be added is approximately from 0.00001 to 0.5% by weight in terms of the concentration of the water-soluble microbicide in the composition.

The clathrate compound of the present invention is helpful in powdering, stabilizing and concentrating the water-soluble microbicide included therein. In addition, since the clathrate compound of the present invention is a reaction product having high selectivity in particular compounds, it may also be used for separating and purifying particular water-soluble microbicides. For instance, Cl-MIT may be separated from a mixture comprising Cl-MIT and its side-product of 2-methyl-4-isothiazolin- 3-one (hereinafter referred to as "MI"), though such separation has heretofore been difficult. This is accomplished by making only Cl-MIT selectively included in a host compound to give a clathrate compound, and then by separating the thus-included Cl-MIT from the clathrate compound. In this way, a high-purity Cl-MIT may be isolated from the mixture. To separate a water-soluble microbicide such as Cl-MIT from the clathrate compound including it, the following methods may be employed.

(1) The clathrate compound is dipped in water.

(2) The clathrate compound is dissolved in an organic solvent and then water is added thereto, whereby only the host compound is made precipitated.

According to these methods, the water-soluble microbicide included in the clathrate compound dissolves out into water, and it is recovered as its aqueous solution.

When a water-soluble microbicide is formed into a clathrate compound with the above-mentioned phenolic compound acting as the host compound, according to the present invention, it becomes solid so that its handleability is much improved. In addition, the dissolution of the microbicide component into water from the clathrate compound is significantly lowered, and the toxicity and the skin-stimulating property of the microbicide are reduced. Moreover, the microbicide in the clathrate compound is prevented from reacting with any other substance to lower its microbicidal activity during its use. Further, the heat-resistant stability of the microbicide is improved, as it is included in the clathrate compound.

For these reasons, the clathrate compound of the present invention may be used effectively as a slow-release microbicide whereby the microbicidal activity may be maintained for a long period of time.

In addition, since the clathrate compound of the present invention is helpful in powdering, stabilizing and concentrating the water-soluble microbicide therein and since the host compound selectively includes the water-soluble microbicide therein, the present invention is also useful for separating and purifying water-soluble microbicides.

In particular, when Cl-MIT is used as the water-soluble microbicide, the present invention provides an excellent microbicidal product.

Preferably, the clathrate compound of the present invention is most stable when used in the form of a microbicidal composition containing the compound along with a predetermined amount of a nitroalcoholic compound.

The present invention will be described in more detail by means of the following examples, which are not intended to restrict the scope of the present invention.

EXAMPLE 1

Production of Clathrate Compound of Cl-MIT and 2,4-Di-Ter-Butylphenol (by Methanol Solvent Method)

500 g of a water-soluble microbicide consisting essentially of Cl-MIT (Cl-MIT concentration: 10.4% by weight) were extracted with 200 g of chloroform, and the solvent in the chloroform layer was removed by distillation to separate Cl-MIT. The yield was 50 g, and the product contained 2 to 3% by weight of MI.

0.69 g (3.34 mmol) of 2,4-di-tert-butylphenol were put int a sample bottle and dissolved in 10 ml of methanol therein. 0.5 g (3.34 mmol) of the previously separated Cl-MIT were added thereto and mixed. After mixing, the mixture was left as it was, thereby removing the solvent thererfrom by natural drying to make crystals precipitated. The thus-obtained crystals were separated, washed with 2 ml of water and then dried.

The product was analyzed by IR spectrography and NMR spectrography, and the Cl-MIT content in the product was measured by HPLC. As a result, the product was identified to be a clathrate compound of 2,4-di-tert-butylphenol/Cl-MIT of nearly 2/1 (by mol), having a Cl-MIT content of 25.83% by weight.

EXAMPLE 2

Production of Clathrate Compound of Cl-MIT and 4,4'-Ethylidene-Bisphenol (By Methanol Solvent Method)

The same process as in Example 1 was repeated, except that 0.5 g (3.34 mmol) of Cl-MIT and the same molar amount of 4,4'-ethylidene-bisphenol were used, and the product was analyzed in the same manner as in Example 1. The product was identified to be a clathrate compound of 4,4'-ethylidene-bisphenol/Cl-MIT of nearly 1/1 (by mol), having a Cl-MIT content of 37.84% by weight.

EXAMPLE 3

Production of Clathrate Compound of Cl-MIT and 2,4-Di-Tert-Butylphenol (By Water Solvent Method)

1.436 g (6.95 mmol) of 2,4-di-tert-butylphenol and 10 g of an aqueous microbicidal solution consisting essentially of Cl-MIT (Cl-MIT concentration: 10.4% by weight, Cl-MIT content: 1.04 g (6.95 mmol)) were mixed and reacted, and left overnight. The crystals thus formed were separated from the aqueous layer, washed with 2 ml of water and then dried.

The product was analyzed by IR spectrography and NMR spectrography, and the Cl-MIT content in the product was measured by HPLC. As a result, the product was identified to be a clathrate compound of 2,4-di-tert-butylphenol/Cl-MIT of nearly 2/1, having a Cl-MIT content of 25.8% by weight.

TEST EXPERIMENT 1

Test for Thermal Stability (at 40° C.) of Cl-MIT In Its Clathrate Compound 10 g of each of the clathrate compounds obtained by the methanol solvent method in Examples 1 and 2 were put into a screw-cap bottle, which was then sealed. These bottles were set in a thermostat at 40° C. At intervals, the content in each bottle was sampled and analyzed by HPLC to determine the Cl-MIT content in the clathrate compound. From the data measured and the initial Cl-MIT content in the fresh compound, the retention percentage of Cl-MIT remained in the sampled clathrate compound was obtained. The results are shown in Table 1 below.

For comparison, only Cl-MIT was tested in the same manner as above to obtain the retention percentage thereof. The results are also shown in Table 1.

TABLE 1

| | | | Retention Percentage of Cl-MIT (%) | | |
|---|---|---|---|---|---|
| No. | Host Compound | Molar Ratio (guest/host) | initial value | after 1 week | after 1 month |
| 1 | 2,4-Di-tert-butylphenol | 1/2 | 100.0 | 97.6 | 97.2 |
| 2 | 4,4'-Ethylidene-bisphenol | 1/1 | 100.0 | 96.2 | 96.5 |
| 3 | (Cl-MIT in the nude) | — | 100.0 | 0.0 | 0.0 |

From the test results, it has been confirmed that Cl-MIT in the nude blackened and decomposed in one week while the clathrate compound including Cl-MIT did not.

TEST EXPERIMENT 2

Measurement of Cl-MIT Released into Water (at 25° C.) From Clathrate Compound Including It Each of the clathrate compounds obtained in Examples 1 and 2 was mixed with water to prepare an aqueous mixture having a Cl-MIT concentration of 3% by weight. The thus-prepared mixtures were kept in a thermostat tank at 25° C. and sampled at intervals. Each sample was passed through a 0.45 μm-millipore filter to thereby separate the clathrate compound from the aqueous phase. Then, the Cl-MIT concentration in the thus-separated aqueous phase was measured by HPLC, from which the amount of Cl-MIT released into water was determined.

The amount of the clathrate compound tested, the amount of water added to the compound, and the amount of Cl-MIT released into water are shown in Table 2.

For comparison, only Cl-MIT was tested in the same manner as above to obtain its amount dissolved in water. The results are also shown in Table 2.

bicide clathrated by a phenolic compound, and it is helpful in powdering, stabilizing and concentrating the water-soluble microbicide therein. In addition, the present inven-

TABLE 2

| No. | Host Compound | Amount (g) Clathrate Compound | Amount (g) Water | Cl-MIT Concentration in Sample (wt. %) | Cl-MIT Concentration in Water (mg/liter)(*1) | Amount of Cl-MIT Released into Water (mg/liter)(*2) after 1 day | after 1 week | after 3 weeks | after 1 month |
|---|---|---|---|---|---|---|---|---|---|
| 4 | 2,4-Di-tert-butylphenol (Cl-MIT content: 25.83 wt. %) | 5.784 | 44.223 | 3 | 33940 | 721 (21.%) | 700 (21%) | 681 (2.0%) | 664 (2.0%) |
| 5 | 4,4'-Ethylidene-bisphenol (Cl-MIT content: 37.84 wt. %) | 3.137 | 36.829 | 3 | 32564 | 335 (1.0%) | 327 (1.0%) | 351 (1.1%) | 330 (1.0%) |
| 6 | Cl-MIT | | | | 30000 (100%) | | | | |

(*1) This means the Cl-MIT concentration in water, resulting from complete release of all Cl-MIT from the clathrate compound sample tested.
(*2) The parenthesized value means the percentage of the released Cl-MIT (as the ratio of the released Cl-MIT to the total Cl-MIT in the fresh clathrate compound).

From the test results, it has been confirmed that the release of Cl-MIT into water from the clathrate compound including it was significantly reduced.

TEST EXAMPLE 3

To the clathrate compound produced in Example 2, containing Cl-MIT included with 4,4'-ethylidene-bisphenol, was added 2-bromo-2-nitro-1,3-propanediol in such an amout as indicated in Table 3 below. The resulting mixture was suspended in water at 60° C. in an amount of 1% by weight in terms of the concentration of Cl-MIT therein. Time-dependent variation in the free Cl-MIT concentration in water and that in the total Cl-MI concentration were measured. The results obtained are shown in Table 3. For comparison, the clathrate compound to which 2,2- 2-bromo-2-nitro-1,3-propanediol had not been added was tested in the same manner as above, and the results obtained are also shown in Table 3.

From Table 3, it is obvious that the addition of 2-bromo-2-nitro-1,3-propanediol resulted in the improvement in the stability of the Cl-MIT-including clathrate compound in water.

TABLE 3

| No. | Amount of 2-bromo-2-nitro-1,3-propanediol (wt. %) | Time | Total Cl-MIT (wt. %) | Free Cl-MIT (ppm) |
|---|---|---|---|---|
| 7 | 0.05 | start | 1.09 | 416 |
|   |      | after 2 weeks | 1.10 | 208 |
|   |      | after 3 weeks | 1.08 | 234 |
| 8 | 0.02 | start | 1.11 | 412 |
|   |      | after 2 weeks | 1.09 | 184 |
|   |      | after 3 weeks | 1.08 | 204 |
| 9 | 0.005 | start | 1.11 | 388 |
|   |       | after 2 weeks | 0 | 0 |
|   |       | after 3 weeks | 0 | 0 |
| 10 | 0 | start | 1.11 | 338 |
|    |   | after 2 weeks | 0 | 0 |
|    |   | after 3 weeks | 0 | 0 |

As described in detail in the above, the clathrate compound of the present invention has a water-soluble microbicide clathrated by a phenolic compound, and it is helpful in powdering, stabilizing and concentrating the water-soluble microbicide therein. In addition, the present invention is also useful for separating and purifying water-soluble microbicides. Moreover, the present invention, thus providing a water-soluble microbicide as its clathrate compound, has the following advantages:

(1) Since the active ingredient included in the clathrate compound may be slowly released into water from the compound, its microbicidal activity may be maintained for a prolonged period of time.

(2) Since the compound is solid, it may be shaped into tablets, etc. Thus, the handling of the compound is easy.

(3) Since the toxicity and the skin-stimulating property of the microbicide in the compound are lowered, the environment using the microbicide is improved and the safe use of the microbicide is ensured.

(4) The thermal stability of the microbicide in the compound may be elevated, resulting in little thermal decomposition of the microbicide.

(5) An active ingredient is prevented from reacting with any other substances to lower its microbicidal activity.

Thus, the industrial importance of the present invention is obvious.

In particular, the present invention preferably uses Cl-MIT as the water-soluble microbicide to be included in the clathrate compound, thus most advantageously displaying the effects.

In addition, the clathrate compound of the present invention is extremely stable when used in the form of a microbicidal composition containing the compound along with a predetermined amount of a nitroalcoholic compound.

While the invention has been described in detail and with reference to specific embodiments thereof, it will be apparent to one skilled in the art that various changes and modifications can be made therein without departing from the spirit and scope thereof.

What is claimed is:

1. A clathrate compound composed of 5-chloro-2-methyl-4-isothiazolin- 3-one as a water-soluble microbicide and a phenolic compound selected from a group consisting of 4,4'-ethylidenebisphenol, 2,4'-isopropylidenebisphenol, 2,2'-vinylidene bisphenol, 4,4'-isobutylidenebisphenol, 2,6'-sec-butylidenebisphenol, 2,4-di-tert-butylphenol, 2,6-di-tert-butylphenol, 2,4-di-propylphenol and 2-propyl-4-tert-butylphenol.

2. The clathrate compound as claimed in claim 1, in which molar ratio of the water-soluble microbicide to the bisphenolic compound is from 1:0.2 to 1:5.

3. The clathrate compound as claimed in claim 1, in which molar ratio of the water-soluble microbicide to the phenolic compound is from 1:0.2 to 1:5.

4. A microbicidal composition containing a clathrate compound claimed in claim 1 and a nitroalcoholic compound having 2–6 carbon atoms.

5. A microbicidal composition containing a clathrate compound as claimed in claim 1 and 2-bromo-2-nitro-1,3-propanediol.

6. The microbicidal composition as claimed in claim 4, which contains a nitroalcoholic compound in an amount of from 0.1 to 5% by weight relative to the clathrate compound.

7. A method for microbicidal treatment, in which a clathrate compound claimed in claim 1 is added to water to be treated therewith.

8. The method as claimed in claim 7, in which the clathrate compound is added to water in an amount of from 0.00001 to 0.5% by weight in terms of the concentration of the water-soluble microbicide in said compound.

9. A method for microbicidal treatment, in which a microbicidal composition claimed in claim 4 is added to water to be treated therewith.

10. The method as claimed in claim 9, in which the microbicidal composition is added to water in an amount of from 0.00001 to 0.5% by weight in terms of the concentration of the water-soluble microbicide in said composition.

* * * * *